United States Patent [19]

Winter et al.

[11] Patent Number: 5,741,868

[45] Date of Patent: Apr. 21, 1998

[54] OLEFIN POLYMERIZATION PROCESS BY USING A SUBSTITUTED INDENYL CONTAINING METALLOCENE CATALYST

[75] Inventors: Andreas Winter, Glashütten; Frank Küber, Oberursel; Michael Aulbach, Hofheim; Bernd Bachmann, Eppstein; Robert Klein, Frankfurt am Main; Klaus Kühlein, Kelkheim; Walter Spaleck, Liederbach; Christian Kohlpaintner, Kelkheim, all of Germany

[73] Assignee: Hoechst Aktiengesellschaft, Frankfurt, Germany

[21] Appl. No.: 477,412

[22] Filed: Jun. 7, 1995

Related U.S. Application Data

[62] Division of Ser. No. 360,608, Dec. 21, 1994, Pat. No. 5,543,373.

[30] Foreign Application Priority Data

Dec. 27, 1993 [DE] Germany ............... 43 44 688.4

[51] Int. Cl.$^6$ ........................... C08F 4/64
[52] U.S. Cl. ........................... 526/127; 526/160; 526/904; 526/943; 526/348.2; 526/348.4; 526/348.6; 526/351; 526/352; 502/155; 556/8; 556/11
[58] Field of Search .................. 526/127, 160, 526/904, 943, 348.2, 348.4, 348.6, 351, 352

[56] References Cited

U.S. PATENT DOCUMENTS

| 5,243,001 | 9/1993 | Winter et al. |
| 5,328,969 | 7/1994 | Winter et al. ............ 526/127 |
| 5,329,031 | 7/1994 | Miyake et al. |
| 5,329,033 | 7/1994 | Spaleck et al. ............ 556/53 |
| 5,474,962 | 12/1995 | Takahashi et al. ............ 502/129 |
| 5,602,219 | 2/1997 | Aulbach et al. ............ 526/160 |

FOREIGN PATENT DOCUMENTS

| 1317411 | 5/1993 | Canada. |
| 1319784 | 6/1993 | Canada. |
| 0 302 424 | 7/1988 | European Pat. Off. |
| 0 336 128 | 3/1989 | European Pat. Off. |
| 0 485 822 | 11/1991 | European Pat. Off. |
| 0 498 675 | 8/1992 | European Pat. Off. |
| 0 544 308 | 11/1992 | European Pat. Off. |
| 0 545 303 | 11/1992 | European Pat. Off. |
| 2 241 244 | 8/1991 | United Kingdom. |

OTHER PUBLICATIONS

J. AM. Chem. Soc., 1988, 110, 6255–6256, 6256–6258.
Agnew. Chem. 102 (1990), Brintzinger et al (No English language translation presently available).
J. Am. Chem. Soc. 1987, 109, 6544–6545, 6546.
Chemical Abstract, vol. 120, 1994, p. 20. Preparation of Highly Syndiotactic Olefin Polymers.
Chemical Abstracts, vol. 118, No. 25, p. 901, Synthesis, Molecular Structure . . . Catalysis, 1993.
Chemical Abstracts, vol. 117, No. 14, p. 3, Standardized Polymerization . . . Comparison, 1992.
Chemical Abstract, vol. 116, No. 24, 1992, p. 4, Comparison of Polymerization . . . Methylaluminoxane.
Chemical Abstracts, vol. 121, No. 26, p. 5, "Asymmetric Zirconocene . . . Polymerization", 1994.
Chemical Abstract, vol. 119, No. 18, 1993, p. 20, Manufacture of Branched Polyethylene and Organometallic Catalyst . . . Manufacturing the same.

*Primary Examiner*—David W. Wu
*Attorney, Agent, or Firm*—Connolly & Hutz

[57] ABSTRACT

The present invention relates to a metallocene compound of the formula I

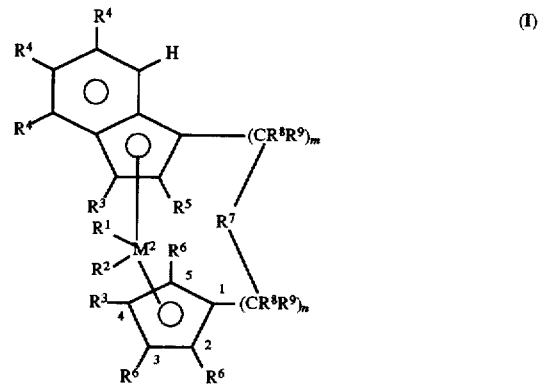

which can advantageously be used as catalyst component for olefin polymerization.

12 Claims, No Drawings

OLEFIN POLYMERIZATION PROCESS BY USING A SUBSTITUTED INDENYL CONTAINING METALLOCENE CATALYST

CROSS REFERENCE TO RELATED APPLICATIONS

This application is a division of application U.S. Ser. No. 08/360,608, filed Dec. 21, 1994 now U.S. Pat. No. 5,543,373, filed by the same inventors.

The invention relates to a metallocene compound which can be advantageously used for the preparation of polyolefins which cover a broad property spectrum. In addition, the metallocene compound of the invention has a high polymerization activity in the industrially interesting temperature range.

The literature discloses the preparation of polyolefins using soluble metallocene compounds in combination with aluminoxanes or other cocatalysts which, owing to their Lewis acidity, can convert the neutral metallocene into a cation and stabilize it.

For example, there has been proposed a specific preactivation method for the metallocene using an aluminoxene, which leads to an increase in the activity of the catalyst system and to a significant improvement in the particle morphology of the polymer (cf. EP 0 302 424). Although the preactivation increases the molecular weight, no significant increase can be achieved. A further, but still not sufficient, increase in the molecular weight was able to be achieved by use of specific heteroatom-bridged metallocenes at high metallocene activity (EP-A 0 336 128).

Furthermore, catalysts based on ethylenebisindenyl hafnium dichloride and ethylenebis(4,5,6,7-tetrahydro-1-indenyl)hafnium dichloride and methylaluminoxane are known, by means of which catalysts relatively high-molecular-weight polypropylenes can be prepared by suspension polymerization (cf. J. A. Ewen et al., J. Am. Chem. Soc. 109 (1987) 6544). However, under industrially relevant polymerization conditions, the particle morphology of the polymers produced in this way is not satisfactory and the activity of the catalysts used is comparatively low. Thus, combined with the high catalyst costs, an inexpensive polymerization is not possible using these systems.

A significant increase in the molecular weight could be achieved by use of metallocenes in which the aromatic π ligands fixed by means of a bridge bear substituents in the 2 position (EP 485 822) or in the 2 and 4,6 positions (EP 545 303).

To meet the demands of inexpensive large-scale production, polymerization has to be carried out at reaction temperatures which are as high as possible, since at higher polymerization temperatures the heat of polymerization generated can be conducted away using less coolant and the reaction can therefore be carried out using significantly smaller dimensions of the cooling water circuit.

In this respect the last-named metallocenes having substituents in the 2 or 4 and 6 positions to the bridge are very effective even at a polymerization temperature of 70° C., but nevertheless the achievable molecular weights at industrially relevant polymerization temperatures (e.g. 70° C.) are still too small for some industrial applications such as, for example, the preparation of polymers for pipes and large hollow bodies and also specific fibres.

Metallocenes having two substituted cyclopentadienyl π ligands such as, for instance, dimethylsilanediyl(2-methyl-4-t-butyl-1-cyclopentadienyl)$_2$ZrCl$_2$ have likewise been proposed as polymerization catalysts (E.-H. Brintzinger et al., Angew. Chem. 102 (1990) 339). However, these systems are in noway convincing with regard to achievable polymer molecular weight, stereospecificity or polymer melting point; furthermore their polymerization activity is very low and the necessary separation of the meso and rac forms obtained from the synthesis is very difficult—highly isotactic polyolefin can only be prepared using the rac form. Furthermore, the meso form is obtained in about the same amount as the rac form, which means that half the chemicals used have to be disposed of and only half the product is usable.

EP-A 0 544 308 proposes catalysts having two different π ligands such as, for instance, isopropylidene(4-methyl-1-cyclopentadienyl)(3-t-butyl-1-indenyl)ZrCl$_2$ which, owing to their asymmetry, possess a priori no meso form and thus circumvent the rac/meso separation problem, but the deficiencies with regard to polymer properties and catalyst activity were not able to be solved.

The work of Ewen et al. (J. Am. Chem. Soc. 110 (1988) 6255) likewise discloses catalysts having two different π ligands such as, for instance, isopropylidene(cyclopentadienyl)(fluorenyl)ZrCl$_2$. However, these asymmetric compounds produce syndiotactic polyolefins. The preparation of isotactic polyolefins is not possible therewith.

It was therefore the object of the invention to provide a catalyst system which avoids the disadvantages of the prior art and, particularly at industrially relevant polymerization temperatures, gives with high polymerization activity, isotactic polyolefins which cover a broad property spectrum, in particular with regard to molecular weights and isotacticities.

It has been found that this object can be achieved by means of a metallocene compound having two differing π ligands which are substituted in a very particular manner.

Owing to their chemical structure, the metallocenes of the invention have no meso form which would have to be separated off in a cost-intensive manner, since only atactic polyolefin can be prepared using meso forms.

In addition, it is possible using the proposed metallocene catalyst concept, by combination of π ligands which have relatively little difference, to provide an inexpensive-to-prepare range of polymerization catalysts for a wide range of polymerization and product requirements.

The invention accordingly provides a metallocene compound of the formula I

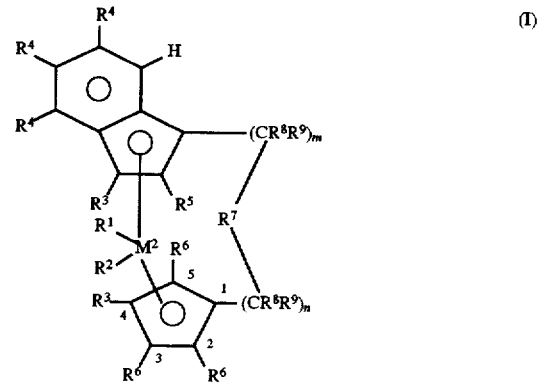

where

M$^2$ is a metal of the group IVb, Vb or VIb of the Periodic Table,

R$^1$ and R$^2$ are identical or different and are a hydrogen atom, a C$_1$–C$_{10}$-alkyl group, a C$_1$–C$_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ are identical or different and are a hydrogen atom, a halogen atom, a $C_1$–$C_{10}$-alkyl group which can be halogenated, a $C_6$–$C_{10}$-aryl group, a $C_2$–$C_{10}$-alkenyl group, a $C_7$–$C_{40}$-arylalkyl group, a $C_7$–$C_{40}$-alkyloxy group, a $C_8$–$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, $R^4$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, or two or more radicals $R^4$ together with the atoms connecting them form a ring system, $R^5$ is a hydrogen atom, a halogen atom, a $C_1$–$C_{10}$-alkyl group which can be halogenated, a $C_6$–$C_{10}$-aryl group, a $C_2$–$C_{10}$-alkenyl group, a $C_7$–$C_{40}$-arylalkyl group, a $C_7$–$C_{40}$-alkyloxy group, a $C_8$–$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, $R^6$ are identical or different and are a hydrogen atom, a halogen atom, a $C_1$–$C_{20}$-alkyl group which can be halogenated, a $C_6$–$C_{30}$-aryl group, a $C_2$–$C_{10}$-alkenyl group, a $C_7$–$C_{40}$-arylalkyl group, a $C_7$–$C_{40}$-alkyloxy group, a $C_8$–$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, $R^7$ is

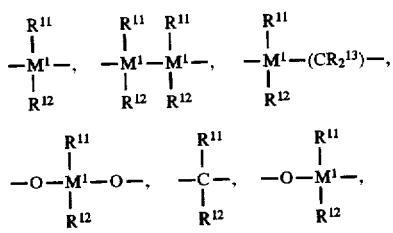

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$14–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, or $R^{11}$ and $R^{12}$ or $R^{11}$ and $R^{13}$ in each case together with the atoms connecting them form a ring, $M^1$ is silicon, germanium or tin, $R^8$ and $R^9$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, or $R^8$ and $R^9$ together with the atoms connecting them form a ring, m and n are identical or different and are zero, 1 or 2, where m plus n is zero, 1 or 2, wherein at least one of the radicals $R^4$ and $R^5$ is not hydrogen.

Alkyl is straight-chain or branched alkyl. Halogen (halogenated) is fluorine, chlorine, bromine or iodine, preferably fluorine or chlorine. Radicals having the same index can be different.

$M^2$ is a metal of the group IVb, Vb or VIb of the Periodic Table, for example titanium, zirconium, hafnium, vanadium, niobium, tantalum, chromium, molybdenum, tungsten, preferably zirconium, hafnium, titanium, particularly preferably Zr.

$R^1$ and $R^2$ are identical or different and are a hydrogen atom, a $C_1$–$C_{10}$-, preferably $C_1$–$C_3$-alkyl group, a $C_1$–$C_{10}$—, preferably $C_1$–$C_3$-alkoxy group, a $C_6$–$C_{10}$—, preferably $C_6$–$C_8$-aryl group, a $C_6$–$C_{10}$—, preferably $C_6$–$C_8$-aryloxy group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group or a halogen atom, preferably chlorine.

$R^3$ is hydrogen, a halogen atom, preferably a fluorine, chlorine or bromine atom, a $C_1$–$C_{10}$—, preferably $C_1$–$C_4$-alkyl group which can be halogenated, a $C_6$–$C_{10}$—, preferably $C_6$–$C_8$-aryl group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group, a —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$—, preferably $C_1$–$C_3$-alkyl group or a $C_6$–$C_{10}$—, preferably $C_6$–$C_8$-aryl group, particularly preferably $R^3$ is hydrogen.

The radicals $R^4$ are identical or different and are a hydrogen atom, a halogen atom, a $C_1$–$C_{20}$—, preferably $C_1$–$C_{10}$-alkyl group, a $C_1$–$C_{20}$-fluoroalkyl group, preferably $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$ fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$-arylalkyl group, a $C_8$–$C_{40}$—, preferably $C_8$–$C_{22}$-arylalkenyl group, a $C_7$–$C_{40}$—, preferably $C_7$–$C_{22}$-alkylaryl group, a —$NR_2^{10}$, —$SR^{10}$, —$OSiR_3^{10}$, —$OR^{10}$, —$SiR_3^{10}$ or —$PR^{10}$ radical, where $R^{10}$ is a halogen atom, preferably a chlorine atom, or a $C_1$–$C_{10}$—, preferably $C_1$–$C_3$-alkyl group or a $C_6$–$C_{10}$—, preferably $C_6$–$C_8$-aryl group, or two or more radicals $R^4$ together with the atoms connecting them form a ring system which is monocyclic or polycyclic.

$R^5$ is a hydrogen atom, a halogen atom, preferably a fluorine, chlorine or bromine atom, a $C_1$–$C_{10}$-, preferably $C_1$–$C_4$-alkyl group which can be halogenated, a $C_6$–$C_{10}$—, preferably $C_6$–$C_8$-aryl group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group, a —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$—, preferably $C_1$–$C_3$-alkyl group or $C_6$–$C_{10}$—, preferably $C_6$–$C_8$-aryl group.

$R^6$ is a hydrogen atom, a halogen atom, preferably a fluorine, chlorine or bromine atom, a $C_1$–$C_{20}$—, preferably $C_1$–$C_{10}$-alkyl group which can be halogenated, a $C_6$–$C_{30}$—, preferably $C_6$–$C_{20}$-aryl group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group, a —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$—, preferably $C_1$–$C_3$-alkyl group or a $C_6$–$C_{10}$—, preferably $C_6$–$C_8$-aryl group.

$R^7$ is

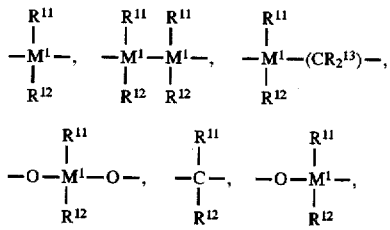

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{20}$—, preferably $C_1$–$C_{10}$-alkyl group, a $C_1$–$C_{20}$-fluoroalkyl group, preferably a $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$-fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$-arylalkyl group, a $C_8$–$C_{40}$—, preferably $C_8$–$C_{22}$-arylalkenyl group or a $C_7$–$C_{40}$—, preferably $C_7$–$C_{22}$-alkylaryl group, or $R^{11}$ and $R^{12}$ or $R^{11}$ and $R^{13}$, in each case together with the atoms connecting them, form a ring.

$M^1$ is silicon, germanium or tin, preferably silicon or germanium.

$R^7$ is preferably =$CR^{11}R^{12}$, =$SiR^{11}R^{12}$, =$GeR^{11}R^{12}$, —O—, —S—, =SO, =$PR^{11}$ or =$P(O)R^{11}$.

$R^8$ and $R^9$ are identical or different and are a hydrogen atom, a halogen atom, a $C_1$–$C_{20}$—, preferably $C_1$–$C_{10}$-alkyl group, a $C_1$–$C_{20}$-fluoroalkyl group, preferably a $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$-fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$-arylalkyl group, a $C_8$–$C_{40}$—, preferably $C_8$–$C_{22}$-arylalkenyl group or a $C_7$–$C_{40}$—, preferably $C_7$–$C_{22}$-alkylaryl group, or $R^8$ and $R^9$ together with the atoms connecting them form a ring.

m and n are identical or different and are zero, 1 or 2, preferably zero or 1, where m plus n is zero, 1 or 2, preferably zero or 1.

The cyclopentadienyl ligand preferably has a radical which is not hydrogen at at least one of the positions adjacent to the —$(CR^8R^9)_n$—$R^7$—$(CR^8R^9)_m$— bridge (2 or 5 position) if the metallocene is to be used for the preparation of a high-molecular-weight highly isotactic polyolefin. For the preparation of low-molecular-weight low-isotacticity polyolefins the cyclopentadienyl ligand is preferably unsubstituted or substituted only in the 3 position.

Preferred metallocenes of the formula (I) for preparing high-molecular-weight, highly isotactic polyolefins are those for which in formula (I)

$M^2$ is zirconium, $R^1$ and $R^2$ are identical or different and are methyl or chlorine, $R^3$ is a hydrogen atom, $R^4$ is a hydrogen atom, a $C_1$–$C_{20}$-alkyl group or a $C_6$–$C_{30}$-aryl group, or two or more radicals $R^4$ together with the atoms connecting them form a ring system, $R^5$ is a hydrogen atom or a $C_1$–$C_{10}$—, preferably $C_1$–$C_4$-alkyl group, $R^6$ is a hydrogen atom, a $C_1$–$C_{10}$-alkyl group, a $C_6$–$C_{20}$-aryl group or a radical $SiR^{10}_3$, where $R^{10}$ is a $C_1$–$C_{10}$-alkyl group, $R^7$ is a radical

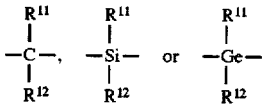

where $R^{11}$ and $R^{12}$ are identical or different and are a $C_1$–$C_{20}$-alkyl group or a $C_6$–$C_{30}$-aryl group, $R^8$ and $R^9$ are identical or different and are a hydrogen atom or a $C_1$–$C_{30}$-alkyl group, m plus n is zero or 1, and at least one of the radicals $R^6$ and also at least one of the radicals $R^5$ and $R^4$ is not hydrogen, in particular those compounds of the formula (I) in which the indenyl ligand is substi- tuted in the 2, 2,4, 2,5, 2,6, 2,4,6, 2,4,5, 2,4,5,6 or 2,5,6 positions, and the cyclopentadienyl ligand is substituted in the 2,3,5 or 2,3,5 positions, where the substituents are preferably $C_1$–$C_{10}$-alkyl , $C_6$–$C_{20}$-aryl or $SiR^{10}_3$ radicals, where $R^{10}$ is a $C_1$–$C_{10}$-alkyl group.

Preferred metallocenes of the formula (I) for preparing low-molecular-weight, low-isotacticity polyolefins are those for which in the formula (I)

$M^2$ is zirconium, $R^1$ and $R^2$ are identical or different and are methyl or chlorine, $R^3$ is hydrogen, $R^4$ is a hydrogen atom, a $C_1$–$C_{20}$-alkyl group or a $C_6$–$C_{30}$-aryl group, or two or more radicals $R^4$ together with the atoms connecting them form a ring system, $R^5$ is a hydrogen atom or a $C_1$–$C_{10}$—, preferably $C_1$–$C_4$-alkyl group, $R^6$ is a hydrogen atom, a $C_1$–$C_{10}$-alkyl group, a $C_6$–$C_{20}$-aryl group or a radical $SiR^{10}_3$, where $R^{10}$ is a $C_1$–$C_{10}$-alkyl group, $R^7$ is a radical

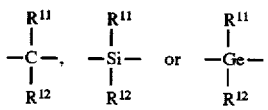

where $R^{11}$ and $R^{12}$ are identical or different and are a $C_1$–$C_{20}$-alkyl group or a $C_6$–$C_{30}$-aryl group, $R^8$ and $R^9$ are identical or different and are a hydrogen atom or a $C_1$–$C_{30}$-alkyl group, m+n is zero or 1, and at least one of the radicals $R^5$ and $R^4$ is not hydrogen, in particular those compounds of the formula (I) in which the indenyl radical is substituted in the 2, 2,4, 2,5, 2,6, 2,4,5, 2,4,5,6 or 2,5,6 positions, and the cyclopentadienyl ligand is unsubstituted or substituted only in the 3 position, where the substituents are preferably $C_1$–$C_{10}$-alkyl, $C_6$–$C_{20}$-aryl or —$SiR^{10}_3$ radicals, where $R^{10}$ is a $C_1$–$C_{10}$-alkyl group.

The nomenclature used here for the site of substitution is as follows:

Cyclopentadienyl ligand: Indenyl ligand:

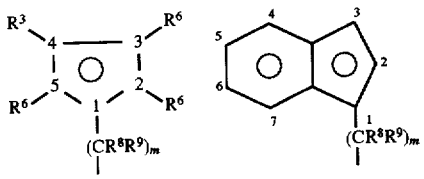

Preferred compounds of the formula (I) for preparing high-molecular-weight, highly isotactic polymers consist of the following molecular fragments a, b, c and d:

a) —$(CR^8R^9)_m$-$R^7$—$(CR^8R^9)_n$— is: dialkylsilanediyl, alkyl(aryl)silanediyl, 1,2-ethanediyl, 1,2-butanediyl, diarylsilanediyl, dialkylmethylene, diarylmethylene, alkyl(aryl)methylene, alkyl(vinyl)silanediyl, aryl (vinyl)silanediyl or dialkylgermyl;

b) $R^4_4R^3R^5$-1-indenyl is: 2-alkyl-4-aryl-1-indenyl, 2,4-dialkyl-1-indenyl, 2,4-diaryl-1-indenyl, 2,4,6-trialkyl-1-indenyl, 2-alkyl-α-acenaphth-1-indenyl, 2-alkyl-4,5-benzo-1-indenyl, 2,5-dialkyl-1-indenyl, 2,6-dialkyl-1-indenyl, 2,5,6-trialkyl-1-indenyl, 2,4,5-trialkyl-1-indenyl, 2-alkyl-1-indenyl, 2-aryl-1-indenyl, 2,6-dialkyl-4-aryl-1-indenyl, 2-alkyl-5-aryl-1-indenyl, 2-alkyl-5,6-diaryl-1-indenyl, 2-alkyl-4,5-diaryl-1-indenyl or 2-alkyl-4,6-diaryl-1-indenyl;

c) $R^6_3R^3$-1-cyclopentadienyl is: 2-alkyl-1-cyclopentadienyl, 3,5-dialkyl-1-cyclopentadienyl, 2,3,5-trialkyl-1-cyclopentadienyl, 2-Si(trialkyl)-1-cyclopentadienyl, 5-Si(trialkyl)-3-alkyl-1-cyclopentadienyl, 2-Si(trialkyl)-3,5-dialkyl-1-cyclopentadienyl, 5-alkyl-3-aryl-1-cyclopentadienyl, 2,5-dialkyl-3-aryl-1-cyclopentadienyl, 2,3-dialkyl-5-aryl-1-cyclopentadienyl, 2-aryl-1-cyclopentadienyl, 5-aryl-3-alkyl-1-cyclopentadienyl, 5-aryl-2,3-dialkyl-1-cyclopentadienyl or 5-alkyl-2,3-diaryl-1-cyclopentadienyl;

d) =$MR^1R^2$ is: =$ZrCl_2$, =$ZrClCH_3$ or =$Zr(CH_3)_2$.

Preferred compounds of the formula (I) for preparing low-molecular-weight, low-isotacticity polymers consist of the following molecule fragments a, b, c and d:

a) —$(CR^8R^9)_m$-$R^7$—$(CR^8R^9)_n$— is: dialkylsilanediyl, alkyl(aryl)silanediyl, 1,2-ethanediyl, 1,2-butanediyl, diarylsilanediyl, dialkylmethylene, diarylmethylene, alkyl (aryl)methylene, alkyl(vinyl)silanediyl, aryl (vinyl)silanediyl or dialkylgermyl;

b) $R^4_4R^3R^5$-1-indenyl is: 2-alkyl-4-aryl-1-indenyl, 2,4-dialkyl-1-indenyl, 2,4-diaryl-1-indenyl, 2,4,6-trialkyl-1-indenyl, 2-alkyl-α-acenaphth-1-indenyl, 2-alkyl-4,5-benzo-1-indenyl, 2,5-dialkyl-1-indenyl, 2,6-dialkyl-1-indenyl, 2,5,6-trialkyl-1-indenyl, 2,4,5-trialkyl-1-indenyl, 2-alkyl-1-indenyl, 2-aryl-1-indenyl, 2,6-dialkyl-4-aryl-1-indenyl, 2-alkyl-5-aryl-1-indenyl, 2-alkyl-5,6-diaryl-1-indenyl, 2-alkyl-4,5-diaryl-1-indenyl or 2-alkyl-4,6-diaryl-1-indenyl;

c) $R^6_3R^3$-1-cyclopentadienyl is: 3-alkyl-1-cyclopentadienyl, 3-aryl-1-cyclopentadienyl, or 1-cyclopentadienyl;

d) =$MR^1R^2$ is: =$ZrCl_2$, =$ZrClCH_3$ or =$Zr(CH_3)_2$.

Examples of compounds of the formula (I) which are particularly suitable for preparing high-molecular-weight, highly isotactic polymers are:

dimethylsilanediyl(2-methyl-4-phenyl-1-indenyl)(2,3,5-trimethyl-1-cyclopentadienyl)$ZrCl_2$,
dimethylsilanediyl(2-methyl-4-phenyl-1-indenyl)(2,3,5-trimethyl-1-cyclopentadienyl)ZrMeCl,
dimethylsilanediyl(2-methyl-4-phenyl-1-indenyl)(2,3,5-trimethyl-1-cyclopentadienyl)$ZrMe_2$,
dimethylsilanediyl(2-methyl-4-phenyl-1-indenyl)(2-methyl-1-cyclopentadienyl)$ZrCl_2$,
dimethylsilanediyl(2-methyl-4-phenyl-1-indenyl)(3,5-dimethyl-1-cyclopentadienyl)$ZrCl_2$,
dimethylsilanediyl (2-methyl-4-phenyl-1-indenyl)(2,5-dimethyl-3-t-butyl-1-cyclopentadienyl)$ZrCl_2$,
1,2-ethanediyl(2-methyl-4-phenyl-1-indenyl)(2,3,5-trimethyl-1-cyclopentadienyl)$ZrCl_2$,
phenyl(methyl)silanediyl(2-methyl-4-phenyl-1-indenyl)(2,3,5-trimethyl-1-cyclopentadienyl)$ZrCl_2$,
diphenylsilanediyl(2-methyl-4-phenyl-1-indenyl)(2,3,5-trimethyl-1-cyclopentadienyl)$ZrCl_2$,
dimethylsilanediyl(2-ethyl-4-phenyl-1-indenyl)(2,3,5-trimethyl-1-cyclopentadienyl)$ZrCl_2$,
dimethylsilanediyl(2,4-diphenyl-1-indenyl)(2,3,5-trimethyl-1-cyclopentadienyl)$ZrCl_2$,
dimethylsilanediyl(2-ethyl-4-(1-naphthyl)-1-indenyl)(2,3,5-trimethyl-1-cyclopentadienyl)$ZrCl_2$,
dimethylgermyl(2-methyl-4-phenyl-1-indenyl)(2,3,5-trimethyl-1-cyclopentadienyl)$ZrCl_2$,
methyl(vinyl)silanediyl(2-methyl-4-phenyl-1-indenyl)(2,3,5-trimethyl-1-cyclopentadienyl)$ZrCl_2$,
phenyl(vinyl)silanediyl(2-methyl-4-phenyl-1-indenyl)(2,3,5-trimethyl-1-cyclopentadienyl)$ZrCl_2$,
dimethylgermyl(2-ethyl-4-(1-naphthyl)-1-indenyl)(2,3,5-trimethyl-1-cyclopentadienyl)$ZrCl_2$,
dimethylsilanediyl(2-methyl-4-(1-naphthyl)-1-indenyl)(2,3,5-trimethyl-1-cyclopentadienyl)$ZrCl_2$,
dimethylsilanediyl (2-methyl-4-(2-naphthyl)-1-indenyl)(2,3,5-trimethyl-1-cyclopentadienyl)$ZrCl_2$,
dimethylsilanediyl(2-methyl-1-indenyl)(2,3,5-trimethyl-1-cyclopentadienyl)$ZrCl_2$,
dimethylsilanediyl(2-methyl-4-isopropyl-1-indenyl)(2,3,5-trimethyl-1-cyclopentadienyl)$ZrCl_2$,
dimethylsilanediyl(2-methyl-4,5-benzo-1-indenyl)(2,3,5-trimethyl-1-cyclopentadienyl)$ZrCl_2$,
dimethylsilanediyl(2-methyl-α-acenaphth-1-indenyl)(2,3,5-trimethyl-1-cyclopentadienyl)$ZrCl_2$,
dimethylsilanediyl(2-methyl-4,6-diisopropyl-1-indenyl)(2,3,5-trimethyl-1-cyclopentadienyl)$ZrCl_2$,
dimethylsilanediyl(2,4,6-trimethyl-1-indenyl)(2,3,5-trimethyl-1-cyclopentadienyl)$ZrCl_2$,
dimethylsilanediyl(2,5,6-trimethyl-1-indenyl)(2,3,5-trimethyl-1-cyclopentadienyl)$ZrCl_2$,
dimethylsilanediyl(2,4,5-trimethyl-1-indenyl)(2,3,5-trimethyl-1-cyclopentadienyl)$ZrCl_2$,
dimethylsilanediyl(2,5-dimethyl-1-indenyl)(2,3,5-trimethyl-1-cyclopentadienyl)$ZrCl_2$ and
dimethylsilanediyl(2,6-dimethyl-1-indenyl)(2,3,5-trimethyl- 1-cyclopentadienyl)$ZrCl_2$.

Examples of the compounds of the formula (I) which are particularly suitable for preparing low-molecular-weight, low-isotacticity polymers are:

dimethylsilanediyl(2-methyl-4,5-benzo-1-indenyl)(3-methyl-1-cyclopentadienyl)$ZrCl_2$,
dimethylmethylene(2-methyl-1-indenyl)(cyclopentadienyl)$ZrCl_2$,
dimethylmethylene(4,5-benzo-1-indenyl)(cyclopentadienyl)$ZrCl_2$,
dimethylgermyl(4,5-benzo-1-indenyl)(cyclopentadienyl)$ZrCl_2$,
dimethylsylanediyl(2-methyl-4,5-benzo-1-indenyl)(clyclopentadienyl)$ZrCl_2$.

dimethylsilanediyl(2-methyl-4-phenyl-1-indenyl)(3-methyl-1-cyclopentadienyl)ZrCl₂, dimethylgermyl(2-methyl-4-phenol-1-indenyl)(cyclopentadienyl)ZrCl₂, dimethylsilanediyl(4-phenyl-1-indenyl)(3-methyl-1-cyclopentadyenyl)ZrCl₂, dimethylsilanediyl(4-phenyl-1-indenyl)(cyclopentadienyl)ZrCl₂, dimethylmethylene(4-phenyl-1-indenyl)(cyclopentadienyl)ZrCl₂ and dimethylsilanediyl(4,5-benzo-1-indenyl)(cyclopentadienyl)ZrCl₂.

The metallocenes of the formula (I) can in principle be prepared according to the following reaction scheme:

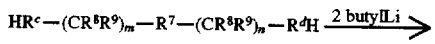
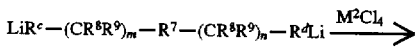

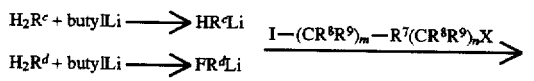

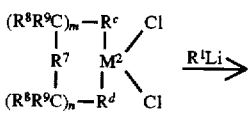

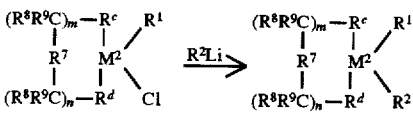

X = Cl, Br, I, O-tosyl;

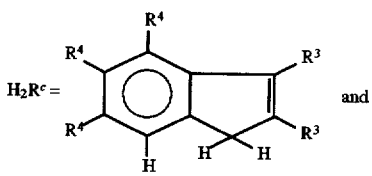

and

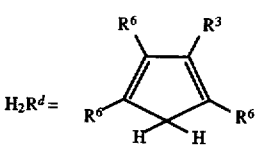

or

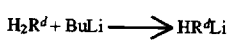

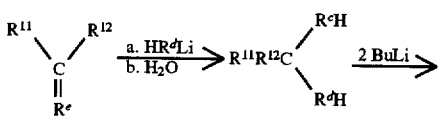

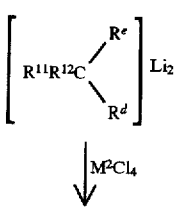

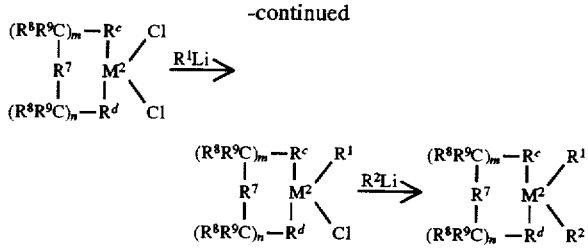

(cf. Journal of Organomet. Chem. (1985) 63–67 and EP-A 320 762).

The present invention also provides a process for preparing an olefin polymer by polymerization of at least one olefin in the presence of a catalyst which contains at least one metallocene as transition metal compound and at least one cocatalysts, wherein the metallocene is a compound of the formula I.

The polymerization can be a homopolymerization or a copolymerization. Preference is given to homopolymerizing or copolymerizing olefins of the formula $R^a$—C=CH—$R^b$, where $R^a$ and $R^b$ are identical or different and are a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene.

In the process of the invention, preference is given to homopolymerizing ethylene or propylene, or copolymerizing ethylene with one or more 1-olefins having 3–20 carbon atoms, such as propylene, and/or one or more dienes having 4–20 carbon atoms, such as 1,3-butadiane. Examples of copolymers are ethylene/propylene copolymers, ethylene/propylene/1,4-hexadiene copolymers, ethylene/propylene/5-ethylidene-2-norbornene copolymers or ethylene/norbornene copolymers.

The process of the invention is particularly suitable for preparing isotactic olefin polymers.

The polymerization is preferably carried out at a temperature of from 0° to 200° C., particularly preferably from 50° to 100° C. The pressure is preferably from 0.5 to 100 bar, in particular from 5 to 64 bar.

The polymerization can be carried out in solution, in suspension or in the gas phase, continuously or batch-wise, and in one or more stages.

The catalyst used in the process of the invention preferably contains one metallocene and one cocatalyst. It is also possible to use mixtures of two or more metallocenes of the invention, in particular for preparing polyolefins having a broad or multimodal molecular weight distribution.

In principle, the cocatalyst in the process of the invention can be any compound which, owing to its Lewis acidity, can convert the neutral metallocene into a cation and stabilize the latter ("labile coordination"). Furthermore, the cocatalyst or the anion formed therefrom should undergo no further reactions with the metallocene cation formed (EP 427 697). Cocatalyst used are preferably aluminum and/or boron compounds.

As aluminum compound, preference is given in the process of the invention to using an aluminoxane which preferably has the formula II

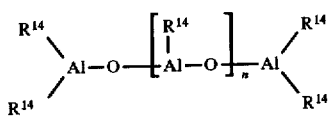

for the linear type and/or the formula III

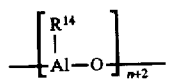

for the cyclic type, where, in the formulae II and III, the radicals $R^{14}$ can be identical or different and are a $C_1$–$C_6$-alkyl group, a $C_1$–$C_6$-fluoroalkyl group, a $C_6$–$C_{18}$-aryl group, a $C_6$–$C_{18}$-fluoroaryl group or hydrogen and n is an integer from 0 to 50, or in place of the aluminoxane a mixture of an aluminoxane with a compound $AlR_3^{15}$, where $R^{15}$ is as defined for $R^{14}$.

Preferably, the radicals $Ry^{14}$ are identical and are methyl, isobutyl, phenyl or benzyl, particularly preferably methyl.

If the radicals $R^{14}$ are different, then they are preferably methyl and hydrogen or alternatively methyl and isobutyl, where hydrogen or isobutyl are preferably present in an amount of 0.01–40% (radicals $R^{14}$). The cocatalyst in the polymerization can be, in place of the aluminoxane, a mixture consisting of aluminoxane and $AlR_3^{15}$, where $R^{15}$ is as defined for $R^{14}$. Preferably, the radicals $R^{15}$ are identical and are methyl, ethyl, isobutyl, phenyl or benzyl.

The aluminoxane can be prepared in various ways by known methods. One of the methods is, for example, reacting an aluminum-hydrocarbon compound and/or a hydridoaluminum-hydrocarbon compound with water (gaseous, solid, liquid or bound, for example as water of crystallization) in an inert solvent (such as toluene). To prepare an aluminoxane having differing alkyl groups $R^{14}$, two different aluminumtrialkyls ($AlR^{14}_3+AlR^{14'}_3$) corresponding to the desired composition are reacted with water (cf. S. Pasynkiewicz, Polyhedron 9 (1990) 429 and EP-A 302 424).

The exact three-dimensional structure of the aluminoxanes is not known (A. R. Barron et al., J. Am. Chem. Soc. 115 (1993) 4971). For example, it is conceivable that chains or rings join to form larger two-dimensional or three-dimensional structures.

Independently of the method of preparation, aluminoxane solutions have in common a varying content of unreacted aluminum starting compound which is present in free form or as an adduct.

It is possible to preactivate the metallocenes with a cocatalyst, in particular aluminoxane, prior to use in the polymerization reaction. This significantly increases the polymerization activity and improves the particle morphology.

The preactivation of the metallocenes is carried out in solution. Preference As here given to dissolving the solid metallocenes in a solution of the aluminoxane in an inert hydrocarbon. Suitable inert hydrocarbons are aliphatic or aromatic hydrocarbons. Preference is given to using toluene or a $C_6$–$C_{10}$-hydrocarbon.

The concentration of the aluminoxane in the solution is preferably in the range from about 1% by weight to the saturation limit, preferably from 5 to 30% by weight, in each case based on the total solution. The metallocenes can be used in the same concentration, but they are preferably used in an amount of $10^{-4}$–1 mole per mole of aluminoxane. The preactivation time is from 1 minute to 60 hours, preferably from 2 to 60 minutes. It is carried out at a temperature of from $-78°$ C. to $100°$ C., preferably from $0°$ to $70°$ C.

The metallocene can (if desired together with a cocatalyst) be applied to a support and/or be prepolymerized. For the prepolymerization, preference is given to using the (or one of the) olefin(s) used in the polymerization.

Suitable supports are, for example, silica gels, aluminum oxides, solid aluminoxane, combinations of aluminoxane on a support such as, for example, silica gel, or other inorganic support materials. Another suitable support material is a polyolefin powder in finely divided form.

A further possible embodiment of the process of the invention comprises using a salt-like boron compound of the formula $R_xNH_{4-x}BR'_4$ or the formula $R_3PHBR'_4$ as cocatalyst in place of or in addition to an aluminoxane. Here x=1, 2 or 3, R=alkyl or aryl, identical or different, and R'=aryl which can also be fluorinated or partially fluorinated. In this case, the catalyst consists of the reaction product of the metallocenes with one of the specified compounds (cf. EP-A 277 004).

To remove catalyst poisons present in the olefin, a purification using an aluminumalkyl, for example $AlMe_3$ or $AlEt_3$ is advantageous. This purification can either be carried out in the polymerization system itself, or the olefin is, prior to addition to the polymerization system, brought into contact with the aluminum compound and subsequently separated off again.

The addition of hydrogen effects an additional strong increase in the polymerization activity.

The total pressure in the polymerization system is from 0.5 to 100 Bar. The polymerization is preferably carried out in the industrially particularly important pressure range from 5 to 64 bar.

The metallocenes are preferably used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The cocatalyst, such as aluminoxane or an aluminoxane/$AlR^{11}_3$ mixture, is preferably used in a concentration of from $10^{-5}$ to $10^{-1}$ mol, preferably from $10^{-4}$ to $10^{-2}$ mol, per $dm^3$ of solvent or per $dm^3$ of reactor volume. However, higher concentrations are also possible in principle.

If the polymerization is carried out as a suspension or solution polymerization, an inert solvent customary for the Ziegler low-pressure process is used. For example, the polymerization is carried out in an aliphatic or cycloaliphatic hydrocarbon; examples which may be mentioned being propane, butane, pentane, hexane, heptane, decane, isooctane, cyclohexane, methylcyclohexane.

Furthermore, it is possible to use a gasoline or hydrogenated diesel oil fraction. Toluene can also be used. Preferably, polymerization is carried out in the liquid monomer.

If inert solvents are used, the monomers are metered in gaseous or liquid form.

The duration of the polymerization is as desired, since the catalyst system of the invention shows only a small time-dependent decrease in the polymerization activity.

The process of the invention can, in particular in the industrially important temperature range from $50°$ to $100°$ C., be used to prepare polyolefins having a high molecular weight and a high isotacticity. These are important, in particular, for the preparation of shaped parts such as films, plates or large hollow bodies (e.g. pipes).

The process of the invention can also be used to prepare polyolefins having a low molecular weight and a low isotacticity, as are important for coatings and adhesive applications.

The metallocene of the invention has a high catalyst activity, in particular at temperatures between $50°$ and $100°$ C. In addition, the complicated separation of the meso form becomes superfluous. Furthermore, combination of different ligands provides metallocenes which give isotactic polyolefins having tailored properties.

In particular, the metallocenes of the invention in supported form give polyolefins having very good powder morphologies.

The following examples are intended to illustrate the invention in greater detail.

Definitions

VN=Viscosity number in cm$^3$/g
$M_w$=Weight-average molecular weight in g/mol (determined by GPC)
$M_w/M_n$=Polydispersity (determined by GPC)
II=Isotactic index (mm+½ mr) (determined by $^{13}$C-NMR)
$n_{iso}$=Isotactic block length (determined by $^{13}$C-NMR)
MFI (230/2.16) Melt flow index determined in accordance with DIN 53735 in dg/min
MFI (230/5) Melt flow index determined in accordance with DIN 53735 in dg/min
m.p.=Melting point determined by DSC in °C. (20° C./min heating and cooling rate)
rac=The structural unit formed by the central atom and the two ligands has approximately $C_s$ symmetry (the fused 6-membered ring of the indenyl ligand is not taken into account in considering the symmetry).
pseudo-rac=The structural unit formed by the central atom and the two ligands has approximately $C_2$ symmetry (the fused 6-membered ring of the indenyl ligand is not taken into account in considering the symmetry).
Rac and pseudo-rac compounds are chiral at the central atom.

All glass apparatus was baked out in vacuo and flushed with argon. All operations were carried out with exclusion of moisture and oxygen in Schlenk vessels. The solvents used were, with the exception of dichloromethane, distilled under argon from a Na/K alloy. Dichloromethane was distilled under argon from CaH$_2$.

EXAMPLE 1

Dimethylsilanediyl(2-methyl-4-phenyl-1-indenyl)(2,3,5-trimethyl-1-cyclopentadienyl)zirconium dichloride (1)

29 ml of a 2.5M solution of butyllithium in hexane were added dropwise at room temperature to a solution of 15 g (73 mmol) of 2-methyl-7-phenylindene in 150 ml of toluene and 7.5 ml of Et$_2$O over a period of 30 minutes and the mixture was subsequently stirred for 2 hours at 40° C. The suspension was subsequently added dropwise at room temperature to a solution of 35.3 ml (290 mmol) of dimethyldichlorosilane in 100 ml of toluene and the mixture was stirred for a further 3 hours at room temperature. The solvent was removed in vacuo and the residue was dried in vacuo (0.1 torr) and subsequently taken up in 200 ml of toluene. To this solution was added dropwise, at room temperature, a suspension of 1,2,4-trimethylcyclopentadienyllithium (prepared by reaction of 7.9 g (73 mmol) of 1,2,4-trimethylcyclopentadiene in 60 ml of toluene and 6 ml of THF at room temperature with 29 ml of a 2.5M solution of butyllithium in hexene end stirring further for 1 hour at 40° C.) over a period of 50 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 400 g of silica gel (hexane/methylene chloride 9:1). This gave 10.3 g (38%) of the ligand system of compound 1 as a colorless oil.

27 ml (74 mmol) of a 20% strength solution of butyllithium in toluene was added dropwise at 50° C. to a solution of 10.0 g (37 mmol) of the ligand system of compound 1 in 50 ml of toluene over a period of 20 minutes and the mixture was subsequently stirred for a further 2 hours at 100° C. After gas evolution had ceased, the mixture was cooled to –40° C. and admixed with 8.6 g (37 mmol) of ZrCl$_4$ and stirred for a further 1 hour at room temperature. It was again cooled to –40° C., admixed with 5 ml of THF and filtered through a G3 Schlenk frit.

The filtrate was evaporated to half its volume and allowed to crystallize at –30° C. The precipitated solid was filtered off, washed three times with 20 ml of hexane each time and subsequently dried. This gave 9 g (46%) of compound (1) as a yellow solid.

$^1$H-NMR (100 MHz, CDCl$_3$): 6.9–7.8 (m, 8H, arom. H and β-H-Ind), 6.4 (s, 1H, H-Cp), 1.9–2.1 (4s, 16H, CH$_3$), 1.0 and 1.1 (2s, 6H, CH$_3$Si).

Mass spectrum: 530 M$^+$, correct disintegration pattern.

EXAMPLE 2

Dimethylsilanediyl (2-methyl-4,5-benzoindenyl) (cyclopentadienyl)zirconium dichloride (2)

111 ml of a 2.5M solution of butyllithium in hexane were added dropwise at room temperature to a solution of 50.1 g (278 mmol) of 2-methyl-4,5-benzoindene (the preparation is described in EP 549 900) in 500 ml of toluene and 25 ml of Et$_2$O over a period of 30 minutes and the mixture was subsequently stirred for a further 2 hours at 40° C. The suspension was subsequently added dropwise at room temperature to a solution of 135 ml (1112 mmol) of dimethyldichlorosilane in 200 ml of toluene and the mixture was stirred for a further 3 hours at room temperature. The solvent was removed in vacuo, the residue was dried in vacuo (0.1 torr) and subsequently taken up in 200 ml of toluene. The suspension is filtered off from lithium chloride and the solvent of the filtrate is removed in vacuo. This gives 43 g (57%) of a red oily product.

17.6 g (64.7 mmol) of dimethyl(2-methyl-4,5-benzoindenyl)chlorosilane were initially charged in 100 ml of THF and a suspension of cyclopentadienyllithium (prepared by reaction of 6.4 g (97.6 mmol) of cyclopentadiene in 50 ml of THF with 39.0 ml (97.6 mmol) of a 2.5M solution of butyllithium in hexane and stirring further for 1 hour at 40° C.) was added dropwise at room temperature over a period of 15 minutes and the mixture was subsequently stirred for a further 2 hours at room temperature. The reaction mixture was admixed with 250 ml of water, the phases were separated and the organic phase was washed with 50 ml of water. The solvents were removed in vacuo and the residue was purified by chromatography on 400 g of silica gel (hexane/methylene chloride 10:1). This gave 10.37 g (53%) of the ligand system of compound (2) as a colorless oil.

7.3 ml (18.3 mmol) of a solution of butyllithium in hexane (2.5M) were added dropwise at room temperature to a solution of 2.64 g (8.7 mmol) of the ligand system of compound 2 in 50 ml of toluene/5 ml of Et$_2$O over a period of 20 minutes and the mixture was subsequently stirred for a further 2 hours at room temperature. After gas evolution had ceased, the mixture was cooled to –40° C., admixed with 1.98 g (8.5 mmol) of ZrCl$_4$ and stirred for a further 1 hour at room temperature. The suspension was filtered through a G3 frit, washed twice with 20 ml of CH$_2$Cl$_2$ and the solvent removed from the filtrate in vacuo. Recrystallization from CH$_2$Cl$_2$ gives 2.39 g (61%) of the metallocene (2).

$^1$H-NMR (300 MHz, CDCl$_3$): δ=8.06 (m, 6H, arom. H); 7.18 (m, 1H, benzoindenyl-H); 6.68 (m, 2H, Cp-H); 5.96 (m, 1H, Cp-H); 5.80 (m, 1H, Cp-H); 2.28 (s, 3H, CH$_3$-benzo.-H); 1.03/0.91 (each s, each 3H, (CH$_3$)$_2$Si).

EXAMPLE 3
Isopropylidene (4,5-benzoindenyl)(cyclopentadienyl) zirconium dichloride (3)

13.8 ml (34.5 mmol) of a 2.5M solution of butyllithium in hexane were added dropwise at 0° C. to a solution of 6.2 g (37.3 mmol) of 4,5-benzoindene (the preparation is described in DE 4139595) in 55 ml of THF over a period of 30 minutes and the mixture was subsequently stirred for a further 2 hours at 40° C. The suspension was subsequently added at −30° C. to a solution of 3.6 g (34.3 mmol) of 6,6-dimethylfulvene in 16 ml of THF. The mixture is allowed slowly to warm up to room temperature in a cold bath and is stirred for a further 3 hours at room temperature. The suspension was admixed with 100 ml of water, the phases were separated and the organic phase was washed with 50 ml of water. The solvents were removed in vacuo and the residue was purified by chromatography on 350 g of silica gel (isohexane/diisopropyl ether 1%). This gave 5.1 g (55%) of the ligand system of compound (3) as a yellow oil.

15.7 ml (39.3 mmol) of a solution of butyllithium in hexene (2.5M) were added dropwise at room temperature to a solution of 5.1 g (18.7 mmol) of the ligand system of compound 3 in 100 ml of Et$_2$O and subsequently stirred for a further 2 hours at room temperature. The suspension is filtered and gives, after drying in vacuo, 6.4 g (17.9 mmol) of the dilithium compound to which one molecule of ether is coordinated. This dilithium compound is added at −78° C. to a suspension of 4.0 g (17.1 mmol) of ZrCl$_4$ in 100 ml of toluene. The mixture is allowed slowly to warm up to room temperature in a cold bath and is stirred for a further 1 hour at room temperature. The suspension was filtered through a G4 frit and washed twice with 40 ml of toluene. The residue was extracted with 500 ml of CH$_2$Cl$_2$ and the filtrate was reduced to 50 ml in vacuo. After isolating the yellow solid formed by filtration and subsequent drying in vacuo, 5.8 g (79%) of the metallocene (3) are obtained as a yellow powder.

$^1$H-NMR (100 MHz, CDCl$_3$): δ=8.18–7.41 (m, 6H, arom. H); 7.22 (m, 1H, benzoindenyl-H); 6.50 (m, 2H, Cp-H); 6.13 (d, 1H, benzoindenyl-H); 5.88 (m, 1H, Cp-H); 5.77 (m, 1H, Cp-H); 2.25/1.98 (each s, each 3H, (CH$_3$)$_2$C).

EXAMPLE 4
Dimethylsilanediyl(4,5-benzoindenyl)(cyclopentadienyl) zirconium dichloride (4)

26.7 ml (66.8 mmol) of a 2.5M solution of butyllithium in hexane were added dropwise at 0° C. to a solution of 11.1 g (66.8 mmol) of 4,5-benzoindens in 120 ml of toluene and 6 ml of Et$_2$O over a period of 30 minutes and subsequently stirred for a further 2 hours at 40° C. The suspension was subsequently added dropwise at room temperature to a solution of 32.4 ml (267 mmol) of dimethyldichlorosilane in 200 ml of toluene and the mixture was stirred for a further 3 hours at room temperature. The suspension is filtered off from the lithium chloride and the solvent of the filtrate is removed in vacuo. This gives 16.8 g (97%) of a yellow oily product.

16.8 g (64.7 mmol) of dimethyl(4,5-benzoindenyl) chlorosilane were initially charged in 80 ml of THF, admixed at room temperature with a solution of 8.5 g (96.5 mmol) of cyclopentadienylsodium in 80 ml of THF and the mixture was subsequently stirred for a further 2 hours at room temperature. The reaction mixture was admixed with 300 ml of water, the phases were separated and the organic phase was washed with 50 ml of water. The solvents were removed in vacuo and the residue was purified by chromatography on 400 g of silica gel (iso-hexane/diisopropyl ether 2%). This gave 14.3 g (77%) of the ligand system of compound 4 as a pale yellow oil.

22.9 ml (58.2 mmol) of a solution of butyllithium in hexane (2.5M) were added dropwise at room temperature to a solution of 8.0 g (27.7 mmol) of the ligand system of compound 4 in 200 ml of Et$_2$O and subsequently stirred for a further 2 hours at room temperature. The suspension was filtered and, after drying in vacuo, gives 9.0 g (24 mmol) of the dilithium compound to which one molecule of ether is coordinated. This dilithium compound is added at −78° C. to a suspension of 5.3 g (22.8 mmol) of ZrCl$_4$ in 140 ml of toluene. The mixture is allowed slowly to warm up to room temperature in a cold bath and is stirred for a further one hour at room temperature. The suspension was filtered through a G4 frit and washed twice with 25 ml of toluene. The residue was extracted with 500 ml of CH$_2$Cl$_2$ and the filtrate was reduced to 50 ml in vacuo. After isolating the yellow solid formed by filtration and subsequent drying in vacuo, 6.3 g (62%) of the metallocene (4) are obtained.

$^1$H-NMR (100 MHz, CDCl$_3$): β=8.10–7.25 (m, 6H, arom. H); 7.41 (m, 1H, benzoindenyl-H); 6.75 (m, 2H, Cp-H); 6.20 (d, 1H, benzoindenyl-H); 5.94 (m, 2H, Cp-H); 1.04/0.88 (each s, each 3H, (CH$_3$)$_2$Si).

EXAMPLE 5
Isopropylidene(2-methylindenyl)(cyclopentadienyl) zirconium dichloride (5)

6.2 ml (15.4 mmol) of a 2.5M solution of butyllithiumin hexane were added dropwise at 0° C. to a solution of 2.0 g (15.4 mmol) of 2-methylindene in 20 ml of THF over a period of 5 minutes and subsequently stirred for a further 2 hours at 40° C. The suspension was subsequently added at −30° C to a solution of 1.6 g (15.4 mmol) of 6,6-dimethylfulvene in 10 ml of THF. The mixture is allowed slowly to warmup to room temperature in a cold bath and is stirred for a further 3 hours at room temperature. The suspension was admixed with 100 ml of water, the phases were separated and the organic phase was washed with 50 ml of water. The solvents were removed in vacuo and the residue was purified by chromatography on silica gel (iso-hexane/diisopropyl ether 1%). This gave 3.2 g (88%) of the ligand system of compound 5 as a yellow oil.

11.4 ml (28.4 mmol) of a solution of butyllithium in hexane (2.5M) were added dropwise at room temperature to a solution of 3.2 g (13.5 mmol) of the ligand system of compound 5 in 90 ml of Et$_2$O and subsequently stirred for a further 2 hours at room temperature. The suspension is filtered and, after drying in vacuo, gives 4.0 g (12.4 mmol) of the dilithium compound to which one molecule of ether is coordinated. This dilithium compound is added at −78° C. to a suspension of 2.7 g (11.8 mmol) of ZrCl$_4$ in 65 ml of toluene. The mixture is allowed slowly to warm up to room temperature in a cold hath and is stirred for a further 1 hour at room temperature. The yellow suspension was filtered through a G4 frit and washed twice with 10 ml of toluene. The residue was extracted with 120 ml of CH$_2$Cl$_2$ and the filtrate was reduced to 15 ml in vacuo. After isolating the resultant yellow solid by filtration and subsequent drying in vacuo, 4.02 g (86%) of the metallocene (5) are obtained as a yellow powder.

$^1$H-NMR (100 MHz, CDCl$_3$): δ=7.80–6.85 (m, 4H, arom. H); 6.62 (s, 1H, indenyl-H); 6.50 (m, 2H, Cp-H); 5.80 (m, 2H, Cp-H); 2.37/2.23/2.12 (each s, each 3H, (CH$_3$)$_2$C or CH$_3$-Ind.).

EXAMPLE 6
Dimethylsilanediyl(2-methyl-4,5-benzoindenyl)(2-methylcyclopentadienyl)zirconium dichloride (6)

111 ml of a 2.5M solution of butyllithiumin hexane were added dropwise at room temperature to a solution of 50.1 g (278 mmol) of 2-methyl-4,5-benzoindene (the preparation is described in EP 549 900) in 500 ml of toluene and 25 ml of Et$_2$O over a period of 30 minutes and subsequently stirred for a further 2 hours at 40° C. The suspension was subsequently added dropwise at room temperature to a solution of 135 ml (1112 mmol) of dimethyldichlorosilane in 200 ml of toluene and the mixture was stirred for a further 3 hours at room temperature. The solvent was removed in vacuo, the residue was dried in vacuo (0.1 torr) and subsequently taken up in 200 ml of toluene. The suspension is filtered off from lithium chloride and the solvent of the filtrate is removed in vacuo. This gives 43 g (57%) of a red oily product.

15.0 g (55 mmol) of dimethyl(2-methyl-4,5-benzoindenyl)chlorosilane were initially charged in 70 ml of THF and a suspension of methylcyclopentadienyllithium (prepared by reaction of 4.85 g (60.5 mmol) of methylcyclopentadiene in 60 ml of THF with 24.2 ml (60.5 mmol) of a 2.5M solution of butyllithium in hexane and further stirring for 1 hour at 40° C.) was added dropwise over a period of 15 minutes and the mixture was subsequently stirred for a further 4 hours at room temperature. The reaction mixture was admixed with 250 ml of water, the phases were separated and the organic phase was washed with 50 ml of water. The solvents were removed in vacuo and the residue was purified by chromatography on 400 g of silica gel (hexane/2% ethyl acetate). This gave 9.92 g (57%) of the ligand system of compound 6 as a colorless oil.

13.2 ml (33.2 mmol) of a 2.5M solution of butyllithium in hexane were added dropwise at room temperature to a solution of 5.0 g (15.8 mmol) of the ligand system of compound 6 in 90 ml of diethyl ether over a period of 20 minutes and subsequently stirred for a further 2 hours at room temperature. The solvent was removed in vacuo and the oily residue was stirred with pentane. The solid formed is filtered off and dried in vacuo. This gives 4.89 g of lithium salt to which 1 equivalent of ether is still coordinated. 3.49 g (15 mmol) of ZrCl$_4$ are initially charged in 100 ml of methylene chloride at −78° C. and admixed with the lithium salt. The mixture is allowed to warm up to room temperature over a period of 12 hours and is stirred for a further 1 hour at room temperature. The suspension was filtered through a G3 frit, washed twice with 20 ml of methylene chloride and the residue on the frit was dried in vacuo. This gives 2.22 g (31%) of the rac compound (6).

$^1$H-NMR (100 MHz, CDCl$_3$): β=8.27–7.04 (m, 8H, arom. H and benzoindenyl-H), 6.80–5.40 (m, 3H, Cp-H), 2.32/2.04 (each s, each 3H, CH$_3$-Cp and CH$_3$-benzo.); 1.04/0.94 (each s, each 3H, (CH$_3$)$_2$Si).

The filtrate was evaporated to ⅕ of its volume and was kept at −30° C. until it crystallized. This gave 1.81 g of the "pseudo-rac" complex (6) as a yellow solid.

$^1$H-NMR (100 MHz, CDCl$_3$): β=8.10–7.14 (m, 8H, arom. H and benzoindenyl-H), 6.53–5.51 (m, 3H, Cp-H), 2.29/2.25 (each s, each 3H, CH$_3$-Cp and CH$_3$-benzo.); 1.10/0.89 (each s, each 3H, (CH$_3$)$_2$Si).

Polymerization Examples

Example A

A dry 24 dm$^3$ reactor was flushed with propylene and charged with 12 dm$^3$ of liquid propylene and 25 cm$^3$ of methylaluminoxane solution in toluene (corresponding to 37 mmol of Al, average degree of oligomerization was n=20). The contents were stirred at 30° C. for 5 minutes at 250 rpm. In parallel thereto, 2.0 mg of dimethylsilanediyl(2-methyl-4-phenyl-1-indenyl)(2,3,5-trimethyl-1-cyclopentadienyl) zirconium dichloride (1) were dissolved in 10 cm$^3$ of methylaluminoxane solution in toluene (17 mmol of Al) and preactivated by being left to stand for 5 minutes. The solution was added to the reactor and polymerization was carried out for 1 hour at 70° C. This gave 1.27 kg of polypropylene. The metallocene activity was 635 kg PP/g metallocene×h. The following properties were determined on the polymer:

VN=275 cm$^3$/g; M$_w$=385 500 g/mol; M$_w$/M$_n$=2.0;

MFI (230/2)=3.9 dg/min; m.p. 157° C; II=98.0%; n$_{iso}$=98.

Example B

Example A was repeated at a polymerization temperature of 50° C. The metallocene activity was 265 kg PP/g metallocene×h.

VN=485 cm$^3$/g; M$_w$=564,000 g/mol; M$_w$/M$_n$=2.1;

MFI (230/5)=0.9 dg/min; m.p. 162° C.; II=98.9%; n$_{iso}$=150.

Example C (Comparative Example)

Example A was repeated using the metallocene rac-dimethylsilanediylbis(2,3,5-trimethyl-1-cyclopentadienyl) zirconium dichloride. The activity achieved was 85 kg PP/g metallocene×h and the polymer had the following properties:

VN=53 cm$^3$/g; M$_w$=46,100 g/mol; M$_w$/M$_n$=2.8;

MFI not measurable, since polymer was too fluid; m.p. 152° C.; II=97.0%.

Examples D to H

A dry 1.5 dm$^3$ reactor was flushed with nitrogen and charged at 20° C with 0.75 dm$^3$ of a de-aromatized petroleum fraction having a boiling range from 100° to 120° C. The gas space of the reactor was then flushed free of nitrogen by pressurizing with 2 bar of ethylene and depressurizing 5 times. 3.75 cm$^3$ of methylaluminoxane solution in toluene (5 mmol of Al, n=18) were then added. While stirring, the reactor was heated to 30° C. (over a period of 15 minutes) and, at a stirring speed of 500 rpm, a total pressure of 5 bar was set by addition of ethylene. In parallel thereto, 0.125 mg of metallocene (for type of compound, see Table 1) was dissolved in 1.25 cm$^3$ of methylaluminoxane solution in toluene (1.67 mmol of Al, m=18) and was completely reacted by being left to stand for 15 minutes. The solution was then added to the reactor, the polymerization system was brought to 70° C. and, by means of appropriate cooling, was left at this temperature for 1 hour. During this time, the pressure was maintained at 5 bar by appropriate addition of ethylene. The polymerization was then stopped by addition of 2 ml of isopropanol, the polymer was filtered off and dried in vacuo. The results of the polymerizations are shown in Table 1.

TABLE 1

Ethylene Polymerizations (Examples D to H)

| Example | Metallocene | Activity [kg PE/g met. × h] | VN [cm³/g] |
|---------|-------------|------------------------------|------------|
| D | Me₂Si(4,5-benzo-1-indenyl) (methylcyclopentadienyl) ZrCl₂ | 98 | 149 |
| E | Me₂Si(4,5-benzo-1-indenyl) (cyclopentadienyl) ZrCl₂ | 120 | 162 |
| F | Me₂C(4,5-benzo-1-indenyl) (cyclopentadienyl) ZrCl₂ | 14 | 59 |
| G | Me₂Bi(2-me-4,5-benzo-1-indenyl) (cyclopentadienyl) ZrCl₂ | 66 | 340 |
| H | Me₂C(2-me-1-indenyl) (cyclopentadienyl) ZrCl₂ | 20 | 75 |

Examples I to M

Example A was repeated at a polymerization temperature of 60° C., but using the metallocenes listed in Table 2. The results of the polymerizations are likewise shown in Table 2.

TABLE 2

Propylene Polymerizations (Examples I to M)

| Example | Metallocene | Activity [kg PE/g met. × h] | VN [cm³/g] |
|---------|-------------|------------------------------|------------|
| I | Me₂Bi(4,5-benzo-1-indenyl) (methylcyclopentadienyl) ZrCl₂ | 97 | 62 |
| J | Me₂Bi(4,5-benzo-1-indenyl) (cyclopentadienyl) ZrCl₂ | 57 | 20 |
| K | Me₂C(4,5-benzo-1-indenyl) (cyclopentadienyl) ZrCl₂ | 17 | 8 |
| L | Me₂Si(2-me-4,5-benzo-1-indenyl) (cyclopentadienyl) ZrCl₂ | 360 | 34 |
| M | Me₂C(2-me-1-indenyl) (cyclopentadienyl) ZrCl₂ | 36 | 10 |

Example N

Example A was repeated, but an additional 3 standard dm³ of hydrogen were introduced into the reactor prior to addition of the propylene.

The metallocene activity was 964 kg PP/g metallocene×h.

The following properties were determined on the polymer:

VN=128 cm³/g; $M_w$=171,500 g/mol; $M_w/M_n$=1.9; MFI (230/2)=83 dg/min; m.p. 158° C.

Example O

Example A was repeated, but the polymerization temperature was 50° C. and during the polymerization time 50 g of ethylene were metered into the reactor (0.8 g ethylene/min metering rate).

This gave 1.17 kg of random copolymer.

The metallocene activity was 585 kg copolymer/g metallocene×h.

VN=298 cm³/g; MFI (230/2)=2.8 dg/min, m.p. 132° C. Ethylene content: 3.8% by weight.

Example P

Example O was repeated using 1-hexene as comonomer. The metallocene activity was 476 kg copolymer/g metallocene×h. The hexene content in the random copolymer thus prepared was 4.8% by weight.

Example Q

Example O was repeated using 4-methyl-1-pentene as comonomer. The metallocene activity was 378 kg copolymer/g metallocene×h, the methylpentene content was 5.3% by weight.

Example R

Example O was repeated, but 250 g of ethylene and 150 ml of 5-ethylidene-2-norbornene were metered into the reactor to prepare a terpolymer rubber. The polymerization temperature was 50° C.

The metallocene activity was 282 kg polymer/g metallocene×h.

The following properties were determined on the polymer:

39.8% by weight ethylene content and 5.4% by weight ethylidenenorbornene content, glass transition temperature $T_g$=−55.4° C.

Example S

Example R was carried out without addition of ethylidenenorbornene, the polymerization temperature was 60° C. and the amount of ethylene used was 500 g. The metallocene activity was 598 kg ethylene-propylene rubber/g metallocene×h.

The following properties were determined on the polymer:

52.2% by weight ethylene content, glass transition temperature $T_g$=−53.9° C.

Example T

A dry 150 dm³ reactor was flushed with nitrogen and charged at 20° C. with 100 dm³ of a de-aromatized petroleum fraction having a boiling range from 100° to 120° C. The gas space was then flushed free of nitrogen by pressurizing with 2 bar of propylene and depressurizing 5 times. After addition of 50 l of liquid propylene, 64 m³ of methylaluminoxane solution in toluene (corresponding to 100 mmol of Al) were added and the reactor contents were heated to 50° C. A hydrogen content in the reactor gas space of 1.5% was set by metering in hydrogen and subsequently kept constant during the entire propylene polymerization time by metering in further amounts (gas chromatography, on-line measurement). 25 mg of the metallocene dimethylsilanediyl (2-methyl-4-phenyl-1-indenyl)(2,3,5-trimethyl-1-cyclopentadienyl)zirconium dichloride were dissolved in 16 cm³ of methylaluminoxane solution in toluene (corresponding to 25 mmol of Al) and, after 15 minutes, added to the reactor.

By means of cooling, the reactor was maintained at a polymerization temperature of 50° C. for 5 hours. After venting hydrogen and propylene to a propylene pressure of 1.5 bar in the reactor, the polymerization was continued after addition of 2.0 kg of ethylene for a further 3 hours at 50° C.

The contents of the reactor were discharged onto a pressure filter, the product was separated off from residual suspension medium by means of steam distillation and was dried for 24 hours at 80° C./200 mbar. This gave 19.3 kg of block copolymer powder, corresponding to a metallocene activity of 96.5 kg copolymer/g metallocene×h. The block copolymer contained 8.9% by weight of ethylene, fractionation gave a content of 19.8% by weight of ethylene/propylene rubber, the glass transition temperature of the rubber was −52.7° C. The MFI (230/2) of the total polymer was 46 dg/min.

Example U
Use of a supported catalyst system
a) Preparation of the supported cocatalyst The supported cocatalyst prepared as described in EP 92 107 331.8 in the following manner in a stainless steel reactor of explosion-protected design having a pumped circulation system of 60 bar pressure rating, with inert gas supply, temperature control by means of jacket cooling and a second cooling circuit via a heat exchanger on the pumped circulation system. The pumped circulation system drew the reactor contents via a connection in the bottom of the reactor using a pump, pressed it into a mixer and through a rising line via a heat exchanger back into the reactor. The mixer was connected in such a way that in the inlet there was a constricted tube cross-section where an increased flow velocity arose and into the turbulence zone of which there was led, axially and counter to the flow direction, an arrow feed line through which, in a pulsed manner, each of a defined amount of water and 40 bar of argon were able to be fed. The reaction was monitored via a sampler on the pumped circuit.

The abovedescribed reactor having a volume of 16 dm$^3$ was initially charged with 5 dm$^3$ of decane under inert conditions. 0.3 dm$^3$ (=3.1 mol) of trimethylaluminum were added at 25° C. 250 g of silica gel SD 3116-30 (Grace AG), which were dried beforehand at 120° C. in an argon fluidized bed, were metered into the reactor through a solids funnel and distributed homogeneously by means of the stirrer and the pumped circulation system. A total amount of 45.9 g of water was added to the reactor over a period of 2 hours in portions of 0.1 cm$^3$, each every 15 seconds. The pressure, arising from argon and the gases evolved, was kept constant at 10 bar by means of pressure regulating valves. After 2 l the water had been introduced, the pumped circulation system was switched off and the stirring was continued for a further 5 hours at 25° C. The solvent was removed by means of a pressure filter and the cocatalyst solid was washed with decane. It was then dried in vacuo. The isolated solid contains 19.2% by weight of aluminum. 15 g of this solid (107 mmol of Al) were suspended in 100 cm$^3$ of toluene in a stirrable vessel and cooled to −30° C. At the same time, 200 mg (0.317 mmol) of Me$_2$Si(2-methyl-4-phenyl-1-indanyl)(2,3,5-trimethyl-1-cyclopentadienyl) ZrCl$_2$ were dissolved in 75 cm$^3$ of toluene and added dropwise to the suspension over a period of 30 minutes. The suspension was slowly warmed up to room temperature while stirring, taking on a red color. It was subsequently stirred for 1 hour at 40° C. and, after cooling to room temperature, the mixture was filtered and the solid was washed 3 times with 100 cm$^3$ of toluene each time and once with 100 cm$^3$ of hexane. The remaining filter residue which was moist with hexane was dried in vacuo. This gave 13.7 g of free-flowing, pale red, supported catalyst. Analysis gave a content of 10.5 mg of zirconocene per gram of catalyst.
b) Polymerization 1.0 g of the catalyst prepared under a) were suspended in 25 cm$^3$ of a de-aromatized petroleum fraction having a boiling range from 100° to 120° C.

In parallel thereto, a dry 24 dm$^3$ reactor was flushed first with nitrogen and subsequently with propylene and was charged with 12 dm$^3$ of liquid propylene and with 1.5 dm$^3$ of hydrogen. 3 cm$^3$ of triisobutylaluminum (12 mmol) were then diluted with 30 ml of hexane, added to the reactor and the mixture was stirred for 15 minutes at 30° C. Subsequently, the catalyst suspension was added to the reactor, the mixture was heated to the polymerization temperature of 80° C. (10° C./min) and the polymerization system was maintained at 80° C. for 1 hour by means of cooling. The polymerization was stopped by addition of 20 ml of isopropanol. The excess monomer was vented, the polymer was dried in vacuo. This gave 2.28 kg of polypropylene powder. The metallocene activity was thus 217 kg PP/g met.×h.

VN=235 cm$^3$/g; M$_w$=305,000 g/mol, M$_w$/M$_n$=2.2;
MFI (230/2)=7.4 dg/min; m.p. 152° C.

Powder morphology: no fines<200 μm, average particle diameter d$_{50}$=650 μm, narrow particle size distribution s=ln (d$_{50}$/d$_{16}$)=0.28, bulk density 485 g/dm$^3$.

We claim:

1. A process for preparing an olefin polymer comprising the step of polymerizing at least one olefin in the presence of a catalyst which contains at least one metallocene as transition metal compound and at least one cocatalyst, wherein the metallocene is a compound of the formula I

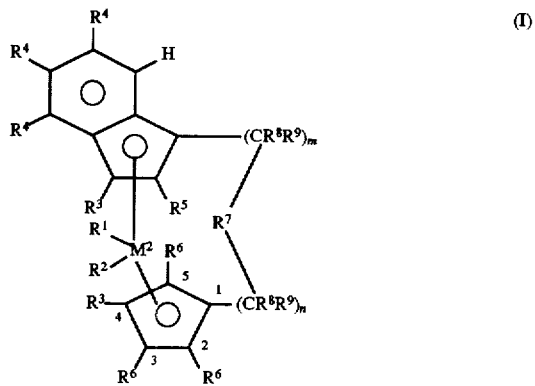

where

M$^2$ is a metal of the group IVb, Vb or VIb of the Periodic Table,

R$^1$ and R$^2$ are identical or different and are a hydrogen atom, a C$_1$–C$_{10}$-alkyl group, a C$_1$–C$_{10}$-alkoxy group, a C$_6$–C$_{10}$-aryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, a C$_8$–C$_{40}$-arylalkenyl group or a halogen atom, R$^3$ are identical or different and are a hydrogen atom, a halogen atom, a C$_1$–C$_{10}$-alkyl group which can be halogenated, a C$_6$–C$_{10}$-aryl group, a C$_2$–C$_{10}$-alkenyl group, a C$_7$–C$_{40}$-arylalkyl group, a C$_7$–C$_{40}$-alkyloxy group, a C$_8$–C$_{40}$-arylalkenyl group, a —NR$_2^{10}$, —OR$^{10}$, —SR$^{10}$, —OSiR$_3^{10}$, —SiR$_3^{10}$ or —PR$_2^{10}$ radical, where R$^{10}$ is a halogen atom, a C$_1$–C$_{10}$-alkyl group or a C$_6$–C$_{10}$-aryl group.

$R^4$ are identical or different and are a hydrogen atom, a halogen atom, a $C_1$-$C_{20}$-alkyl group, a $C_1$-$C_{20}$-fluoroalkyl group, a $C_6$-$C_{30}$-aryl group, a $C_6$-$C_{30}$-fluoroaryl group, a $C_1$-$C_{20}$-alkoxy group, a $C_2$-$C_{20}$-alkenyl group, a $C_7$-$C_{40}$-arylalkyl group, a $C_8$-$C_{40}$-arylalkenyl group, a $C_7$-$C_{40}$-alkylaryl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$-$C_{10}$-alkyl group or a $C_6$-$C_{10}$-aryl group, or two or more radicals $R^4$ together with the atoms connecting them form a ring system, $R^5$ is a hydrogen atom, a halogen atom, a $C_1$-$C_{10}$-alkyl group which can be halogenated, a $C_6$-$C_{10}$-aryl group, a $C_2$-$C_{10}$-alkenyl group, a $C_7$-$C_{40}$-arylalkyl group, a $C_7$-$C_{40}$-alkyloxy group, a $C_8$-$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$-$C_{10}$-alkyl group or a $C_6$-$C_{10}$-aryl group, $R^6$ are identical or different and are a hydrogen atom, a halogen atom, a $C_1$-$C_{20}$-alkyl group which can be halogenated, a $C_6$-$C_{30}$-aryl group, a $C_2$-$C_{10}$-alkenyl group, a $C_7$-$C_{40}$-arylalkyl group, a $C_7$-$C_{40}$-alkyloxy group, a $C_8$-$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$-$C_{10}$-alkyl group or a $C_6$-$C_{10}$-aryl group, $R^7$ is

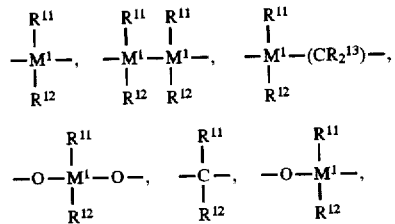

=$BR^{11}$, =$AlR^{11}$, —Ge—, —Sn—, —O—, —S—, =SO, =SO$_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$-$C_{20}$-alkyl group, a $C_1$-$C_{20}$-fluoroalkyl group, a $C_6$-$C_{30}$-aryl group, a $C_6$-$C_{30}$-fluoroaryl group, a $C_1$-$C_{20}$-alkoxy group, a $C_2$-$C_{20}$-alkenyl group, a $C_7$-$C_{40}$-arylalkyl group, a $C_8$-$C_{40}$-arylalkenyl group, a $C_7$-$C_{40}$-alkylaryl group, or $R^{11}$ and $R^{12}$ or $R^{11}$ and $R^{13}$ in each case together with the atoms connecting them form a ring, $M^1$ is silicon, germanium or tin, $R^8$ and $R^9$ are identical or different and are a hydrogen atom, a halogen atom, a $C_1$-$C_{20}$-alkyl group, a $C_1$-$C_{20}$-fluoroalkyl group, a $C_6$-$C_{30}$-aryl group, a $C_6$-$C_{30}$-fluoroaryl group, a $C_1$-$C_{20}$-alkoxy group, a $C_2$-$C_{20}$-alkenyl group, a $C_7$-$C_{40}$-arylalkyl group, a $C_8$-$C_{40}$-arylalkenyl group, a $C_7$-$C_{40}$-alkylaryl group, or $R^8$ and $R^9$ together with the atoms connecting them form a ring, m and n are identical or different and are zero, 1 or 2, where m plus n is zero, 1 or 2, wherein at least one of the radicals $R^4$ and $R^5$ is not hydrogen.

2. The process as claimed in claim 1, wherein the metallocene is supported.

3. The process as claimed in claim 1, wherein the cocatalyst used in an aluminoxane.

4. The process as claimed in claim 1, wherein the metallocene is prepolymerized.

5. A process as claimed in claim 1, wherein the metallocene is prepolymerized and supported.

6. The process as claimed in claim 1, wherein $M^2$ is zirconium, $R^1$ and $R^2$ are identical or different and are methyl or chlorine, $R^3$ is hydrogen, $R^4$ is a hydrogen atom, a $C_1$-$C_{20}$-alkyl group or a $C_6$-$C_{30}$-aryl group, or two or more radicals $R^4$ together with the atoms connecting them form a ring system, $R^5$ is a hydrogen atom or a $C_1$-$C_{10}$-alkyl group, $R^6$ is a hydrogen atom, or a $C_1$-$C_{10}$-alkyl group, a $C_6$-$C_{20}$-aryl group or a radical $SiR_3^{10}$, where $R^{10}$ is a $C_1$-$C_{10}$-alkyl group, $R^7$ is a radical

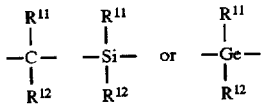

where $R^{11}$ and $R^{12}$ are identical or different and are a $C_1$-$C_{20}$-alkyl group or a $C_6$-$C_{30}$-aryl group, $R^8$ and $R^9$ are identical or different and are a hydrogen atom or a $C_1$-$C_{30}$-alkyl group, m+n is zero or 1, and at least one of the radicals $R^5$ and $R^4$ is not hydrogen.

7. The process as claimed in claim 6, wherein the cocatalyst is an aluminoxane of the formula II

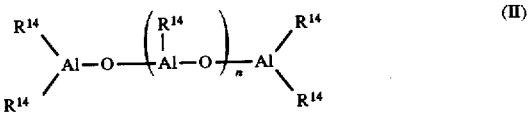

for the linear type and/or the formula (III)

for the cyclic type, where, in the formula II and III, the radicals $R^{14}$ are identical or different and are a $C_1$-$C_6$-alkyl group, a $C_1$-$C_6$-alkyl group, a $C_1$-$C_6$-fluoroalkyl group, a $C_6$-$C_{18}$-aryl group, a $C_6$-$C_{18}$-fluoroaryl group or hydrogen and n is an integer from 0 to 50, or in place of the aluminoxane a mixture of an aluminoxane with a compound $AlR_3^{15}$, where $R^{15}$ is as defined for $R^{14}$.

8. The process as claimed in claim 1, wherein metallocene is selected from the group consisting of dimethylsilanediyl(2-methyl-4-phenyl-1-indenyl)(2,3,5-trimethyl-1-cyclopentadienyl)ZrCl$_2$,
dimethylsilanediyl(2-methyl-4-phenyl-1-indenyl)(2,3,5-trimethyl-1-cyclopentadienyl)ZrMeCl,
dimethylsilanediyl(2-methyl-4-phenyl-1-indenyl)(2,3,5-trimethyl-1-cyclopentadienyl)ZrMe$_2$,
dimethylsilanediyl(2-methyl-4-phenyl-1-indenyl)(2-methyl-1-cyclopentadienyl)ZrCl$_2$,
dimethylsilanediyl(2-methyl-4-phenyl-1-indenyl)(3,5-dimethyl-1-cyclopentadienyl)ZrCl$_2$,
dimethylsilanediyl(2-methyl-4-phenyl-1-indenyl)(2,5-dimethyl-3-t-butyl-1-cyclopentadienyl)ZrCl$_2$,
1,2-ethanediyl(2-methyl-4-phenyl-1-indenyl)(2,3,5-trimethyl-1-cyclopentadienyl)ZrCl$_2$,
phenyl(methyl)silanediyl(2-methyl-4-phenyl-1-indenyl)(2,3,5-trimethyl-1-cyclopentadienyl)ZrCl$_2$,
diphenylsilanediyl(2-methyl-4-phenyl-1-indenyl)(2,3,5-trimethyl-1-cyclopentadienyl)ZrCl$_2$,
dimethylsilanediyl(2-ethyl-4-phenyl-1-indenyl)(2,3,5-trimethyl-1-cyclopentadienyl)ZrCl$_2$,
dimethylsilanediyl(2,4-diphenyl-1-indenyl)(2,3,5-trimethyl-1-cyclopentadienyl)ZrCl$_2$, dimethylsilanediyl(2-ethyl-4-(1-naphthyl)-1-indenyl)(2,3,5-trimethyl-1-cyclopentadienyl)ZrCl$_2$, dimethylgermyl(2-methyl-4-phenyl-1-indenyl)(2,3,5-trimethyl-1-cyclopentadienyl)ZrCl$_2$, methyl(vinyl)silanediyl(2-methyl-4-phenyl-1-indenyl)(2,3,5-trimethyl-1-cyclopentadienyl)ZrCl$_2$, phenyl(vinyl)silanediyl(2-methyl-4-phenyl-1-indenyl)(2,3,5-trimethyl-1-cyclopentadienyl)ZrCl$_2$, dimethylgermyl(2-ethyl-4-(1-naphthyl)-1-indenyl)(2,3,5-trimethyl-1-cyclopentadienyl)ZrCl$_2$, dimethylsilanediyl(2-methyl-4-(1-naphthyl)-1-indenyl)(2,3,5-trimethyl-1-clyclopentadienyl)ZrCl$_2$, dimethylsilanediyl(2-methyl-4-(2-naphthyl)-1-indenyl)(2,3,5-trimethyl-1-cyclopentadienyl)ZrCl$_2$, dimethylsilanediyl(2-methyl-1-indenyl)(2,3,5-trimethyl-1-cyclopentadienyl)ZrCl$_2$, dimethylsilanediyl(2-methyl-4-isopropyl-1-indenyl)(2,3,5-trimethyl-1-cyclopentadienyl)ZrCl$_2$, dimethylsilanediyl(2-methyl-4,5-benzo-1-indenyl)(2,3,5-trimethyl-1-cyclopentadienyl)ZrCl$_2$, dimethylsilanediyl(2-methyl-α-acenaphth-1-indenyl)(2,3,5-trimethyl-1-cyclopentadienyl)ZrCl$_2$, dimethylsilanediyl(2-methyl-4,6-diisopropyl-1-indenyl)(2,3,5-trimethyl-1-cyclopentadienyl)ZrCl$_2$, dimethylsilanediyl(2,4,6-trimethyl-1-indenyl)(2,3,5-trimethyl-1-cyclopentadienyl)ZrCl$_2$, dimethylsilanediyl(2,5,6-trimethyl-1-indenyl)(2,3,5-trimethyl-1-cyclopentadienyl)ZrCl$_2$, dimethylsilanediyl(2,4,5-trimethyl-1-indenyl)(2,3,5-trimethyl-1-cyclopentadienyl)ZrCl$_2$, dimethylsilanediyl(2,5-dimethyl-1-indenyl)(2,3,5-trimethyl-1-cyclopentadienyl)ZrCl$_2$ and dimethylsilanediyl(2,6-dimethyl-1-indenyl)(2,3,5-trimethyl-1-cyclopentadienyl)ZrCl$_2$.

9. The process according to claim 1 wherein the metallocene is selected from the group consisting of dimethylsilanediyl(2-methyl-4,5-benzo-1-indenyl)(3-methyl-1-cyclopentadienyl)ZrCl$_2$, dimethylmethylene(2-methyl-1-indenyl)(cyclopentadienyl)ZrCl$_2$, dimethylmethylene(4,5-benzo-1-indenyl)(cyclopentadienyl)ZrCl$_2$, dimethylgermyl(4,5-benzo-1-indenyl)(cyclopentadienyl)ZrCl$_2$, dimethylsilanediyl(2-methyl-4,5-benzo-1-indenyl)(cyclopentadienyl)ZrCl$_2$, dimethylsilanediyl(2-methyl-4-phenyl-1-indenyl)(3-methyl-1-cyclopentadienyl)ZrCl$_2$, dimethylgermyl(2-methyl-4-phenyl-1-indenyl)(cyclopentadienyl)ZrCl$_2$, dimethylsilanediyl(4-phenyl-1-indenyl)(3-methyl-1-cyclopentadienyl)ZrCl$_2$, dimethylsilanediyl(4-phenyl-1-indenyl)(cyclopentadienyl)ZrCl$_2$, dimethylmethylene(4-phenyl-1-indenyl)(cyclopentadienyl)ZrCl$_2$ and dimethylsilanediyl(4,5-benzo-1-indenyl)(cyclopentadienyl)ZrCl$_2$.

10. The process as claimed in claim 7 wherein $R^{14}$ are identical and are either methyl, isobutyl, phenyl or benzyl.

11. The process as claimed in claim 7 wherein $R^{14}$ are different and are either
  a) methyl and hydrogen or
  b) methyl and isobutyl.

12. The process as claimed in claim 7, wherein $R^{15}$ is methyl, ethyl, isobutyl, phenyl or benzyl.

* * * * *